(12) United States Patent
Bello et al.

(10) Patent No.: US 10,744,298 B1
(45) Date of Patent: Aug. 18, 2020

(54) USER-CONTROLLED URINATION MANAGEMENT SYSTEM

(71) Applicants: Simon Antonio Bello, Walnut Creek, CA (US); Eugenia Maria Correa, Tampa, FL (US); Christopher Lawrence Passaglia, Lutz, FL (US)

(72) Inventors: Simon Antonio Bello, Walnut Creek, CA (US); Eugenia Maria Correa, Tampa, FL (US); Christopher Lawrence Passaglia, Lutz, FL (US)

(73) Assignee: University of South Florida, Tampa, FL (US)

(*) Notice: Subject to any disclaimer, the term of this patent is extended or adjusted under 35 U.S.C. 154(b) by 371 days.

(21) Appl. No.: 15/834,980

(22) Filed: Dec. 7, 2017

Related U.S. Application Data

(60) Provisional application No. 62/434,729, filed on Dec. 15, 2016.

(51) Int. Cl.
| | |
|---|---|
| *A61M 25/00* | (2006.01) |
| *A61B 5/20* | (2006.01) |
| *A61F 2/00* | (2006.01) |
| *A61F 5/445* | (2006.01) |
| *A61F 5/451* | (2006.01) |

(Continued)

(52) U.S. Cl.
CPC ......... *A61M 25/0017* (2013.01); *A61B 5/205* (2013.01); *A61B 5/207* (2013.01); *A61F 5/451* (2013.01); *A61B 5/204* (2013.01); *A61F 2/0036* (2013.01); *A61F 5/445* (2013.01);

(Continued)

(58) Field of Classification Search
CPC ...... A61M 25/0017; A61M 2210/1078; A61M 2210/1085; A61M 2210/1089; A61M 1/0001; A61M 1/0019; A61M 1/0021; A61B 5/204; A61B 5/205; A61B 5/208;

(Continued)

(56) References Cited

FOREIGN PATENT DOCUMENTS

| | | |
|---|---|---|
| EP | 0185809 A1 | 7/1986 |
| EP | 2810616 A1 | 12/2014 |
| WO | WO-2016154457 A1 * | 9/2016 ........... A61B 5/6874 |

OTHER PUBLICATIONS

AMS 800 Urinary Control System for Male Patients, American Medical Systems, Inc., 2014, 40 pages.

(Continued)

*Primary Examiner* — Ophelia A Hawthorne
*Assistant Examiner* — Heather K Barnwell
(74) *Attorney, Agent, or Firm* — Smith & Hopen, P.A.; Steven M. Forte; Nilay J. Choksi

(57) ABSTRACT

An implantable and programmable device for bladder fluid management. Several urological conditions hinder normal urinary evacuation. For instance, urinary retention impedes fluid drainage, which can lead to severe complications. On the other hand, urinary incontinence exposes the patients to frequent fluid leakage that can be difficult to manage. The treatment for these conditions are only partially effective and only address the symptoms but not the cause. The current system allows the user to bypass the nonfunctional portion of the urinary tract and urinate normally. The device is user-controlled and can be manually activated to release fluid at will. A notification system alerts the patient when fluid levels are elevated and require drainage. The current system provides patients with an effective solution to manage irregular bladder function.

10 Claims, 3 Drawing Sheets

(51) Int. Cl.
    *A61M 3/02*         (2006.01)
    *A61M 25/02*       (2006.01)

(52) U.S. Cl.
    CPC ..... *A61M 3/027* (2013.01); *A61M 2025/0206* (2013.01); *A61M 2025/0213* (2013.01)

(58) Field of Classification Search
    CPC .......... A61B 2018/00505; A61B 2018/00507; A61B 5/6874; A61F 2/0036
    See application file for complete search history.

(56) References Cited

OTHER PUBLICATIONS

Hocking, M.G., Non-Catheter simple, non-invasive, bladder draining method with no running costs, Wholeistic Healing Publications, Jan. 2014, vol. 14, No. 1.

\* cited by examiner

USER-CONTROLLED URINATION MANAGEMENT SYSTEM

CROSS-REFERENCE TO RELATED APPLICATIONS

This nonprovisional application claims priority to U.S. Provisional Patent Application No. 62/434,729, entitled "User-Controlled Urination Management System", filed Dec. 15, 2016 by the same inventors, the entirety of which is incorporated herein by reference.

BACKGROUND OF THE INVENTION

1. Field of the Invention

This invention relates, generally, to urinary incontinence and urinary retention. More specifically, it relates to devices that assist in the evacuation of urine through the urinary tract during an impedance of flow through the urinary tract.

2. Brief Description of the Prior Art

Urinary Retention

Chronic urinary retention, or ischuria, is a medical condition where patients are partially or completely unable to empty their bladder. This condition is especially common among men, with studies concluding that 4.5 to 6.8 per 1,000 men over 40 years old present urinary retention. Statistical incidence significantly increases with age, as men over 70 present a 10% chance of developing the condition, while a man over 80 sees his odds increase to 30%. The condition occurs when an obstructive or inflammatory process impedes normal fluid flow through the urinary tract. The most common cause of urinary retention is benign prostatic hyperplasia (BPH), which accounts for over half of the cases. The condition presents an important clinical challenge as its management practices are poorly defined and most prospective trials are not properly inclusive in their subject selection, possibly due to high risk of complications. These issues have left numerous patients across the globe without a viable solution. In most cases, patients must self-catheter multiple times a day in order to release the urine produced by their bodies. This process can be highly uncomfortable and time consuming. If urine is not released, increased pressure is exerted in the kidneys, potentially resulting in permanent organ failure.

Urinary Incontinence

Urinary incontinence is caused by the weakening or loss of sphincter control in the urinary tract, resulting in an involuntary leakage of urine. Although the condition is common among the elderly, estimates project that 30% of people in the US suffer from the condition. Studies have shown that incontinence is not just a medical condition but can also have detrimental emotional and psychological effects that disrupt the patient's social life. Current treatments are based on chemicals that relax the bladder muscles and increase the volume of urine that the bladder can retain. However, these treatments do not address the cause and can only provide partial relief of the symptoms.

Other Urological Conditions

Conditions such as bladder cancer can permanently damage the ability of the bladder to perform as a urine reservoir. The disease requires patients to go through a surgical procedure to replace the bladder with an artificial reservoir or one formed of bowel tissue. An internal conduct, called a stoma, is implanted to provide external access to the new fluid pool. In most cases the patient is required to self-intubate through the stoma and manually empty the pouch every 4-6 hours. Failure to do so can result in leakage or infection, which could lead to kidney failure and pouchitis (inflammation of the reservoir). To avoid these complications, the patient must ensure that drainage is done in a timely manner, preferably before fluid levels reach high values.

Non-Urinary Conditions where Fluid is to be Drained

There are a multitude of conditions, similar to those described above, where a pressure is built up within a sac and fluid within that sac needs to be drained. For instance, survey studies have found an increased incidence of shoulder bursitis among elderly members of the general population. The condition is characterized by inflammation of the sac located between tissues in our joints (bursa). It can present itself in the shoulder, elbow, hip and knee due to chronic injuries or as a natural part of the aging process. The symptoms range from joint stiffness to acute pain in the area. In chronic conditions where extreme inflammation is experienced by the patient, periodic drainage of the joint may be necessary. This process can be painful and requires recurrent visits to the doctor's office. Cortisone shots are often administered to treat the condition, offering significant relief. However, in most cases the symptoms return over time.

Attempts have been made to overcome the difficulties previously described. Examples include European Patent Application No. EP2810616; European Patent Application No. EP0185809; AMS 800 Urinary Control System for Male Patients; and Hocking, M. G. (2010). Non-catheter simple noninvasive bladder draining method with no costs. Indian Journal of Urology: IJU: Journal of the Urological Society of India, 26(2), 296-298. However, none are completely effective in providing a system for continuously monitoring pressure/urine levels based on intra-sac/bladder pressure and notifying a user thereof when the pressure should be relieved or the urine should be drained.

Accordingly, what is needed is an improved user-controlled urination or pressure management system. However, in view of the art considered as a whole at the time the present invention was made, it was not obvious to those of ordinary skill in the field of this invention how the shortcomings of the prior art could be overcome.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

The long-standing but heretofore unfulfilled need for an improved system for relieving urinary retention and incontinence is now met by a new, useful, and nonobvious invention.

In an embodiment, the current invention is a user-controlled urination management system for bypassing a site of obstruction along a urinary tract of a user. The system includes a superior catheter, a pressure transducer, a fluid pump, an inferior catheter, a microcontroller, and a notification module. On one end, the superior catheter is chronically implanted into the user's bladder, and on its opposite end, it is directly or indirectly coupled to the pressure transducer. The transducer is in communication with the interior of the bladder through the superior catheter, and it continuously monitors intra-bladder pressure via the superior catheter placed in the user's bladder. The pump has inlet and outlet ports, where the inlet port is coupled to an end of the superior catheter and the outlet port is coupled to an end of the inferior catheter. The opposite end of the inferior catheter is chronically implanted into the user's urethra at a position distal to the site of obstruction along the user's urinary tract.

The microcontroller is in electrical communication with the pressure transducer and with the pump. The microcontroller receives a pressure signal from the pressure transducer, where the pressure signal indicates the intra-bladder pressure. It converts the pressure signal to an intra-bladder urine volume level, where the intra-bladder pressure and the intra-bladder urine volume level have a direct relationship to each other. The notification module outputs a notification to user pertaining to the intra-bladder pressure and/or the intra-bladder urine volume level. In operation, when the pump is actuated by the user, urine flows from the user's bladder, into the superior catheter, through the pump, into the inferior catheter, and into the urethra, thus bypassing the site of obstruction during output of the urine from the user.

The pressure transducer may be a piezoresistive strain gauge disposed on an alumina ceramic substrate and covered by a silicone gel coating.

The pump may be a micro-pump. Alternatively or in addition, the pump may include a piezoelectric diaphragm in combination with a passive check valve to steadily move fluid. As a result of an increase in voltage generated by the microcontroller, the piezoelectric membrane downwardly deforms, resulting in a displacement of the urine out of the pump in the direction defined by the passive check valve. As a result of a decrease in voltage generated by the microcontroller, the piezoelectric membrane upwardly deforms, drawing the urine into the pump.

The microcontroller may amplify the pressure signal and eliminate vibrational noise due to user movement. Further, the microcontroller may be programmed with a correlation between the intra-bladder pressure and the intra-bladder urine volume level, such that the microcontroller establishes a pressure threshold beyond which the microcontroller directs the notification module to output the notification to the user. When the user subsequently actuates the pump, the microcontroller can use a general-purpose input/output channel to modulate a voltage signal that activates the pump and initiates fluid flow therethrough.

The notification module may include a miniature vibrational motor in the microcontroller that is triggered with an analog signal outputted by the microcontroller. Alternatively, the notification module may include a wireless protocol that causes a mobile device to vibrate or emit an audible signal.

In a separate embodiment, the current invention is a fluid flow management system for controlling flow of a fluid from a sac within a patient, wherein the sac is a reservoir for the fluid. The system includes a first catheter, a pressure transducer, a fluid pump, a second catheter, a microcontroller, and a notification module. On one end, the first catheter is chronically implanted into the user's sac, and on its opposite end, it is directly or indirectly coupled to the pressure transducer. The transducer is in communication with the interior of the sac through the first catheter, and it continuously monitors intra-sac pressure via the first catheter disposed in the user's sac. The pump has inlet and outlet ports, where the inlet port is coupled to an end of the first catheter and the outlet port is coupled to an end of the second catheter.

The microcontroller is in electrical communication with the pressure transducer and with the pump. The microcontroller receives a pressure signal from the pressure transducer, where the pressure signal indicates the intra-sac pressure. It converts the pressure signal to an intra-sac urine volume level, where the intra-sac pressure and the intra-sac urine volume level have a direct relationship to each other. The notification module outputs a notification to user pertaining to the intra-sac pressure and/or the intra-sac urine volume level. In operation, when the pump is actuated by the user, fluid flows from the user's sac, into the first catheter, through the pump, and through the second catheter.

The pressure transducer may be a piezoresistive strain gauge disposed on an alumina ceramic substrate and covered by a silicone gel coating.

The pump may be a micro-pump. Alternatively or in addition, the pump may include a piezoelectric diaphragm in combination with a passive check valve to steadily move fluid. As a result of an increase in voltage generated by the microcontroller, the piezoelectric membrane downwardly deforms, resulting in a displacement of the fluid out of the pump in the direction defined by the passive check valve. As a result of a decrease in voltage generated by the microcontroller, the piezoelectric membrane upwardly deforms, drawing the fluid into the pump.

The microcontroller may amplify the pressure signal and eliminate vibrational noise due to user movement. Further, the microcontroller may be programmed with a correlation between the intra-sac pressure and the intra-sac fluid volume level, such that the microcontroller establishes a pressure threshold beyond which the microcontroller directs the notification module to output the notification to the user. When the user subsequently actuates the pump, the microcontroller can use a general-purpose input/output channel to modulate a voltage signal that activates the pump and initiates fluid flow therethrough.

The notification module may include a miniature vibrational motor in the microcontroller that is triggered with an analog signal outputted by the microcontroller. Alternatively, the notification module may include a wireless protocol that causes a mobile device to vibrate or emit an audible signal.

In an embodiment, the first and second catheters are urinary catheters that are chronically implanted in a bladder of the patient and a urethra of the patient, thus bypassing a site of obstruction in the urethra during output of urine from the user.

In yet another embodiment, the current invention is a user-controlled urination management system for bypassing a site of obstruction along a urinary tract of a user. The system may include any one or more—or even all—of the foregoing features and characteristics.

As it pertains to urinary retention, it is an object of the present invention to provide a system that allows patients to bypass the obstructed portion of the urinary tract and release fluid normally and at will.

As it pertains to urinary incontinence, it is an object of the present invention to provide a device that can be implemented in patients with urinary incontinence as a way to bypass the affected portion of the urinary tract and prevent fluid from leaving the bladder involuntarily. The urethra can be surgically blocked during implantation to prevent leakage, allowing the invention to have full control over volume levels in the bladder. Users will then have the ability to urinate normally.

As it pertains to other urological conditions, it is an object of the present invention to provide a system that offers an alternative treatment to the stoma conduit implantation. The integration of continuous volume measurement of the pouch with fluid evacuation through the pump ensures that patients empty their artificial bladder timely and effectively, avoiding plausible complications. The system can be used to automatize urinary diversion to an external reservoir or to allow for normal urine flow through the urinary tract.

As it pertains to non-urinary, chronic conditions where fluid (liquid or gas) is to be drained, it is an object of the present invention to provide a system that can ease the symptoms experienced by the user/patient. A small cannula could be permanently implanted in the affected bursa to continuously monitor pressure in the joint. A controller would then use pressure information to infer when there is an excess of fluid and use a pump to progressively drain the area. The fluid could be dumped into a small disposable reservoir taped to the outside of the skin. The draining process would be gradual so that fluid levels never reach the point of pain receptor stimulation. The patient could replace the reservoir daily, avoiding time consuming trips to the doctor and, more importantly regaining full mobility without pain.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

Figures 1A, 1B:
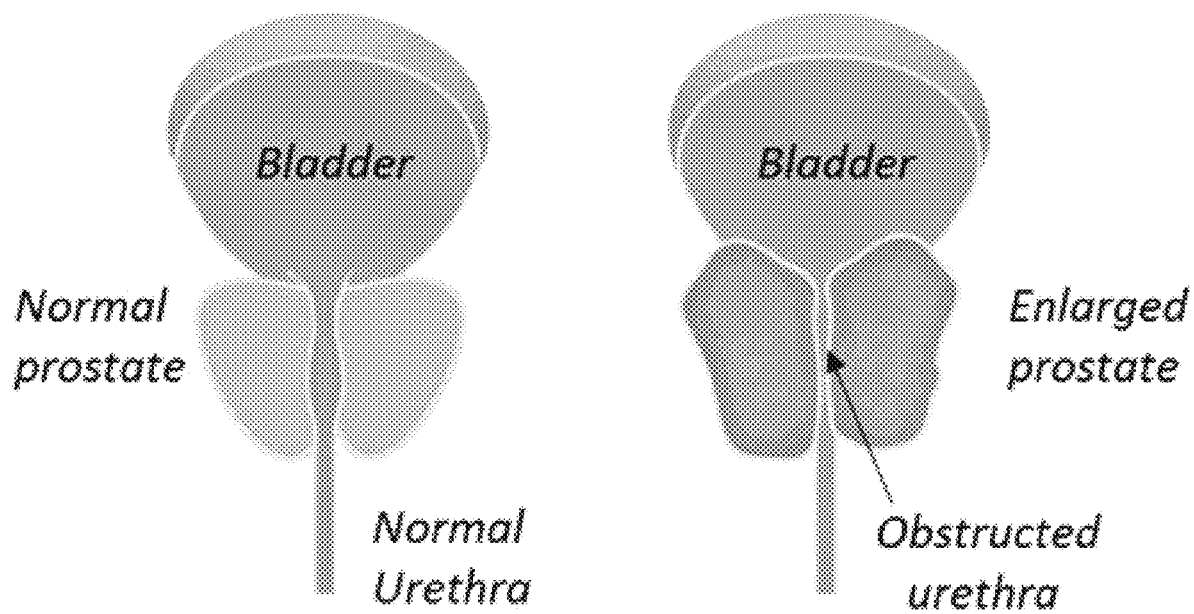
FIG. 1A depicts a normal urinary tract. A healthy prostate lies behind the urethra, allowing the release of urine from the bladder.
FIG. 1B depicts an obstructed urinary tract in males. Prostate enlargement can cause the inflamed tissue to compress the urethral conduct and block fluid outflow

As used in this specification and the appended claims, the singular forms "a", "an", and "the" include plural referents unless the content clearly dictates otherwise. As used in this specification and the appended claims, the term "or" is generally employed in its sense including "and/or" unless the context clearly dictates otherwise, FIGS. 1A-1B are schematics of the lower urinary tract. Under normal conditions (FIG. 1A), the bladder acts as a reservoir that holds urine produced by the kidneys, while the urethra acts as an outflow conduit for the release of fluid. In cases of urinary retention (FIG. 1B), the urethra is obstructed by an inflammatory process (e.g., prostate enlargement) that hinders or prevents fluid flow through the urethra. In an embodiment, the current invention is a pressure-sensitive micro-pump that assists in the evacuation of urine through the urinary tract. The system is intended for use in urological conditions, where patients lose the ability to effectively control their bladder, such as with urinary retention, urinary incontinence, and bladder replacement, among others.

Figure 2A:
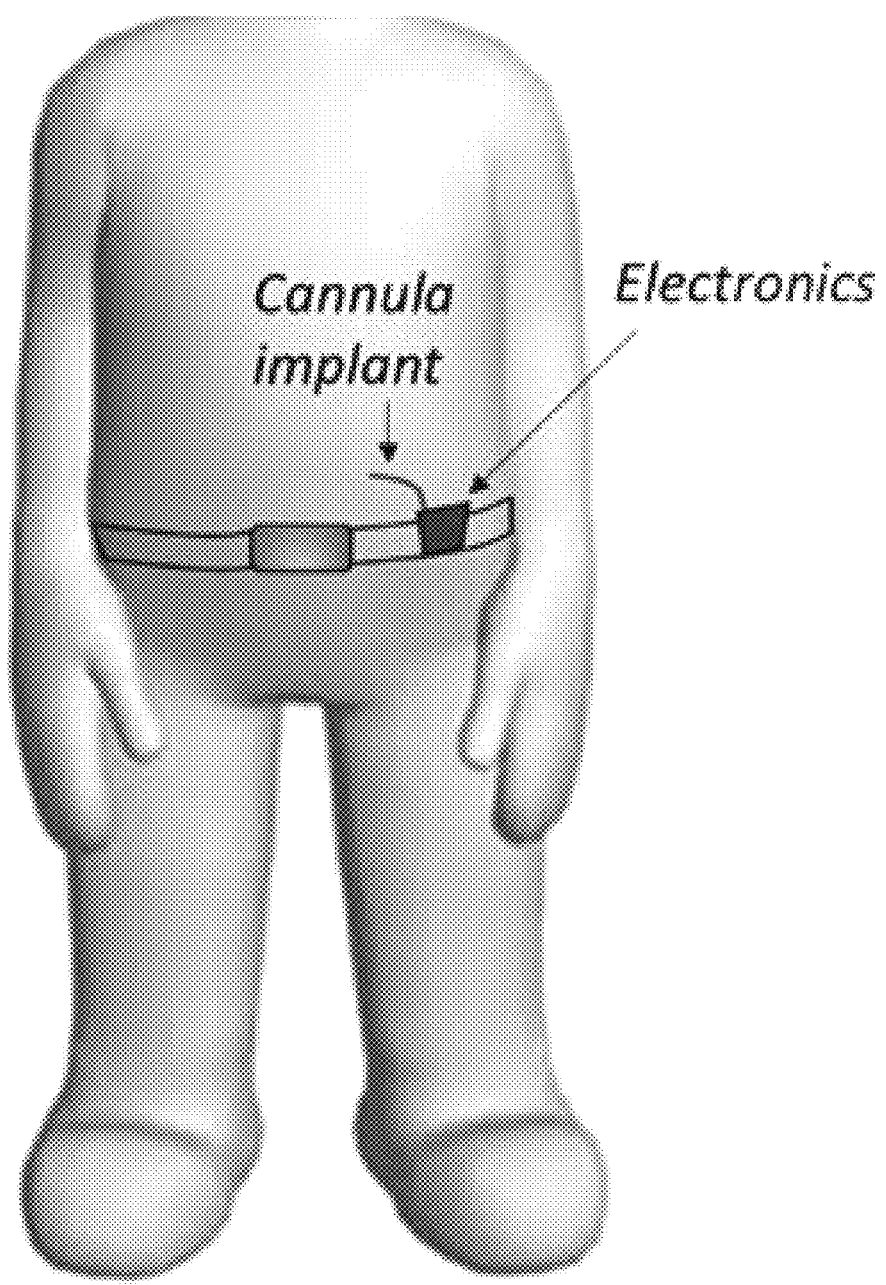
FIG. 2A is an exterior view of a urine release control system, according to an embodiment of the current invention.
Figure 2B:
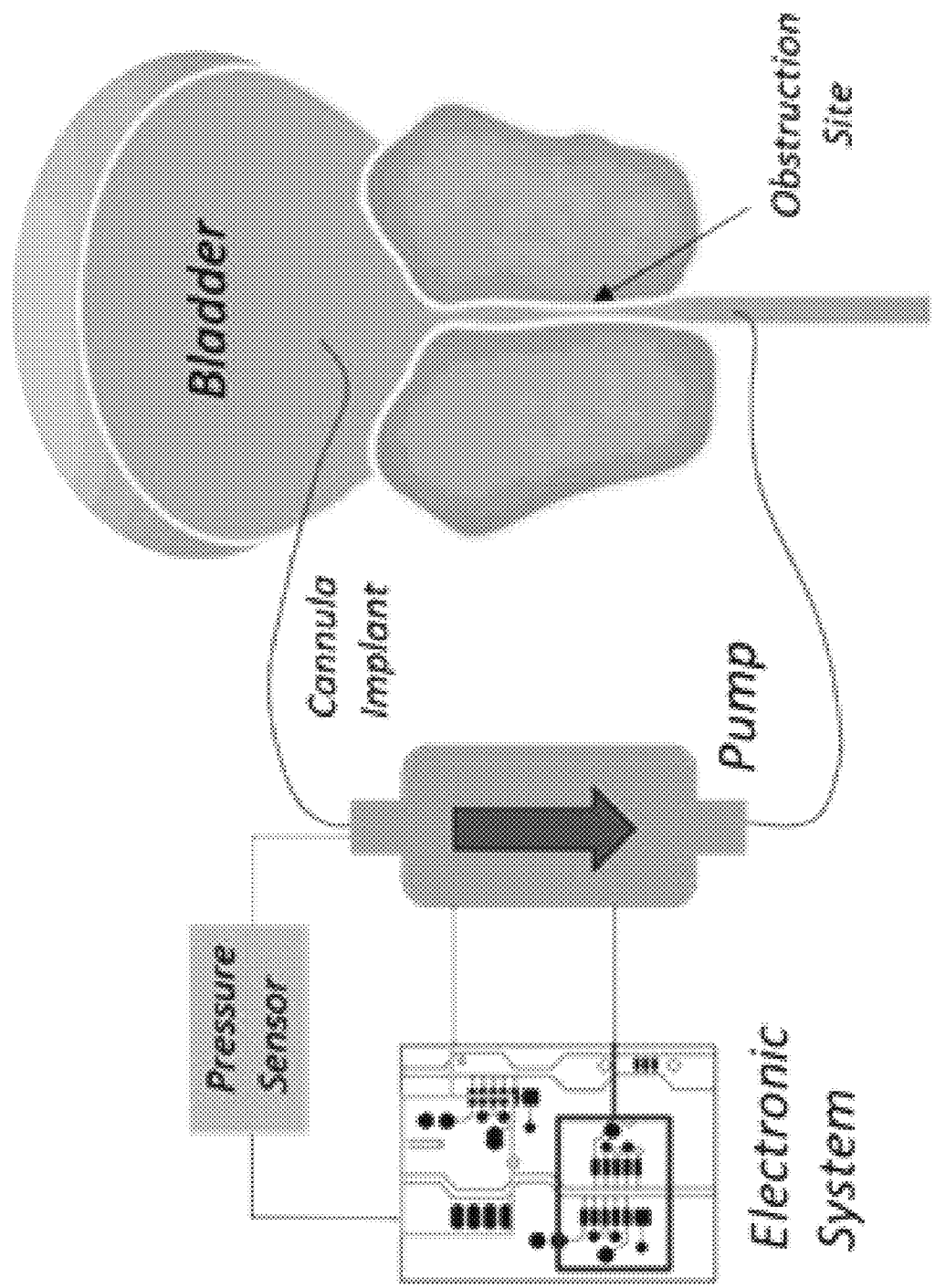
FIG. 2B is a cross-sectional schematic of a urine release control system, according to an embodiment of the current invention.

FIGS. 2A-2B are schematics of an embodiment of the current system. A small, superior catheter is chronically implanted into the bladder on one end, and is coupled directly or indirectly on its opposite end to a pressure sensor/transducer and an inlet port of a pump. A small, inferior catheter is coupled directly or indirectly on one end to an outlet port of the pump, and is chronically implanted into the urethra on its opposite end. The inferior catheter is implanted in the urethra at a position distal to (i.e., past or inferior to) the site of obstruction along the urinary tract (see FIG. 2B).

The pressure transducer continuously monitors intra-bladder pressure via the superior catheter disposed in the patient's bladder. The pressure transducer subsequently transmits the signal indicating intra-bladder pressure to an electronic/control system including specialized circuitry that converts this pressure signal to urine volume levels within the bladder. Intra-bladder pressure and intra-bladder urine volume levels have a direct relationship with each other, such that as pressure increases, volume levels increase as well. This correlation is inputted into the electronic system, either as one or more threshold levels that indicate whether the bladder should be drained or as multiple specific pressure levels correlating to multiple specific volume levels. In either scenario, the electronic system uses the pressure signal to determine fluid volumes within the bladder.

In the former scenario where the pressure threshold is set and indicates whether the bladder should be drained, when pressure levels reach the pre-determined threshold, the system notifies the user when urine levels are high, using any sensory mechanism (e.g., beep, vibration, display, etc.). Manual activation of the pump then initiates fluid release. Specifically, once the patient reaches a restroom facility, the patient actuates the pump (e.g., via toggling a switch on the pump), causing fluid to be pulled/withdrawn from the bladder via the superior catheter, through the pump, through the inferior catheter, and into the urethra, effectively bypassing the site/portion of the urinary tract that is obstructed/non-functional and allowing the patient to urinate normally.

The electronic system (and circuitry included therein) can be externally located (e.g., worn on the patient's belt, as in FIG. 2A) or internally located (e.g., implanted subcutaneously into the patient). The electronic system includes a power source, such as a battery, for operation. Batteries can be recharged as needed with a wired connection. Alternatively, batteries can be wirelessly recharged through RF or inductive energy transfer by placing a small source next to the system while the patient rests or sleeps. Any suitable battery or other power source known in the art may be used, along with any recharging mechanism.

EXAMPLE

In an embodiment, the current system includes five (5) primary components: a catheter, a pressure sensor, a controller including specialized circuitry, a notification system, and a micro-pump. The detailed design of each component is dependent on the planned usage of the system, and thus is adjustable as would be understood by one of ordinary skill in the art. For example, the size of the pump can scale with the volume of fluid that it must accommodate, which in turn, can influence the drive signal that the controller outputs, and so forth.

Catheter

Urinary catheters come in a variety of materials, such as rubber, plastic (PVC), silicone and latex. These catheters are well known in the art and have been used for urinary release and diversion. They have been proven useful and harmless when properly installed and used. Any suitable urinary catheter can be used herein.

Pressure Transducer/Sensor

The pressure sensor is a piezoresistive strain gauge disposed on an alumina ceramic substrate and covered by a silicone gel coating that protects the electronic components from fluid condensation in the line. The transducer is equipped with multiple gauges that allow for temperature compensation in the range of about 0-85° C. Other transducer designs (e.g., capacitive transduction) are also contemplated herein. As such, any suitable pressure sensor may be used herein.

Electronic Circuitry

Pressure signals are amplified and filtered to eliminate vibrational noise due to user movement, and these signals are transmitted to a small programmable microcontroller unit. A custom digital program loaded into the microcontroller uses stored calibration information and current pressure signals to determine volume levels, and the program compares them to the predetermined threshold. When the threshold level is reached, the microcontroller triggers the notification system. When the user activates drainage functions, the circuit uses general-purpose input/output channels to modulate a voltage signal that activates the pump and initiates fluid flow therethrough.

Notification System

Any notification mechanism known in the art may be used herein. For instance, a miniature vibrational motor included in the circuitry can be triggered with an analog signal outputted by the microcontroller. Alternatively, a BLUETOOTH module can be used to communicate with a bracelet or smartphone that vibrates or emits audible signals. Similarly, wireless protocols can be implemented to pair with commonly-used smartphones or fitness trackers.

Pump

The miniature pump uses two piezoelectric diaphragms in combination with passive check valves to steadily move fluid. The voltage generated by the microcontroller causes a downward deformation of the pump's piezoelectric membrane, resulting in a displacement of fluid out of the pump in the direction defined by the valve. Alternatively, when voltage decreases, the membrane experiences an upward deformation that draws fluid from the reservoir into the pump. Oscillation between high and low voltages generates steady flow rates. Alternatively but similarly, miniature peristaltic or piston-operated pumps can also be implemented and driven with an analog or digital signal modulated by the microcontroller.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A user-controlled urination management system for bypassing a site of obstruction along a urinary tract of a user, comprising:
    a superior catheter having a first end and a second end, the first end of the superior catheter configured to be chronically implanted into a bladder of the user;
    a pressure transducer coupled directly or indirectly to the second end of the superior catheter, the pressure transducer for communication with an interior of the bladder through the superior catheter, wherein the pressure transducer is configured to continuously monitor intra-bladder pressure via the superior catheter disposed in the user's bladder;
    a pump having an inlet port and an outlet port, the inlet port of the pump coupled to the second end of the superior catheter;
    an inferior catheter having a first end and a second end, the first end of the inferior catheter coupled to the outlet port of the pump, the second end of the inferior catheter configured to be chronically implanted into a urethra of the user at a position distal to the site of obstruction along the urinary tract of the user;
    a microcontroller in electrical communication with the pressure transducer and with the pump, wherein the microcontroller receives a pressure signal from the pressure transducer, the pressure signal indicating the intra-bladder pressure,
    the microcontroller converting the pressure signal to an intra-bladder urine volume level, where the intra-bladder pressure and the intra-bladder urine volume level have a direct relationship to each other; and
    a notification module that outputs a notification to the user, the notification pertaining to the intra-bladder pressure and/or the intra-bladder urine volume level,
    whereby upon the pump being actuated by the user, urine flows from the user's bladder, into the superior catheter, through the pump, into the inferior catheter, and into the urethra, thus bypassing the site of obstruction during output of the urine from the user.

2. A system as in claim 1, wherein the microcontroller is programmed with a correlation between the intra-bladder pressure and the intra-bladder urine volume level, such that the microcontroller establishes a pressure threshold beyond which the microcontroller directs the notification module to output the notification to the user.

3. A system as in claim 1, wherein the pump is a micro-pump.

4. A system as in claim 1, wherein the pump includes a piezoelectric diaphragm in combination with a passive check valve to steadily move fluid, wherein
- as a result of an increase in voltage generated by the microcontroller, the piezoelectric membrane downwardly deforms, resulting in a displacement of the urine out of the pump in the direction defined by the passive check valve, and
- as a result of a decrease in voltage generated by the microcontroller, the piezoelectric membrane upwardly deforms, drawing the urine into the pump.

5. A system as in claim 1, wherein the microcontroller amplifies the pressure signal and eliminates vibrational noise due to user movement.

6. A system as in claim 1, wherein as a result of the user actuating the pump, the microcontroller uses a general-purpose input/output channel to modulate a voltage signal that activates the pump and initiates fluid flow therethrough.

7. A system as in claim 1, wherein the pressure transducer is a piezoresistive strain gauge disposed on an alumina ceramic substrate and covered by a silicone gel coating.

8. A system as in claim 1, wherein the notification module includes a miniature vibrational motor in the microcontroller that is triggered with an analog signal outputted by the microcontroller.

9. A system as in claim 1, wherein the notification module includes a wireless protocol that causes a mobile device to vibrate or emit an audible signal.

10. A user-controlled urination management system for bypassing a site of obstruction along a urinary tract of a user, comprising:
- a superior catheter having a first end and a second end, the first end of the superior catheter configured to be chronically implanted into a bladder of the user;
- a pressure transducer coupled directly or indirectly to the second end of the superior catheter, the pressure transducer for communication with an interior of the bladder through the superior catheter, wherein the pressure transducer is configured to continuously monitor intra-bladder pressure via the superior catheter disposed in the user's bladder;
- a micro-pump having an inlet port and an outlet port, the inlet port of the pump coupled to the second end of the superior catheter;
- an inferior catheter having a first end and a second end, the first end of the inferior catheter coupled to the outlet port of the pump, the second end of the inferior catheter configured to be chronically implanted into a urethra of the user at a position distal to the site of obstruction along the urinary tract of the user;
- a microcontroller in electrical communication with the pressure transducer and with the pump, wherein the microcontroller receives a pressure signal from the pressure transducer, the pressure signal indicating the intra-bladder pressure,
- the microcontroller converting the pressure signal to an intra-bladder urine volume level, where the intra-bladder pressure and the intra-bladder urine volume level have a direct relationship to each other,
- wherein the microcontroller amplifies the pressure signal and eliminates vibrational noise; and
- a notification module that outputs a notification to the user, the notification pertaining to the intra-bladder pressure and/or the intra-bladder urine volume level,
- wherein the notification module includes a wireless protocol that causes a mobile device to vibrate or emit an audible signal,
- wherein the microcontroller is programmed with a correlation between the intra-bladder pressure and the intra-bladder urine volume level, such that the microcontroller establishes a pressure threshold beyond which the microcontroller directs the notification module to output the notification to the user,
- whereby upon the pump being actuated by the user, urine flows from the user's bladder, into the superior catheter, through the pump, into the inferior catheter, and into the urethra, thus bypassing the site of obstruction during output of the urine from the user,
- wherein as a result of the user actuating the pump, the microcontroller uses a general-purpose input/output channel to modulate a voltage signal that activates the pump and initiates fluid flow therethrough.

* * * * *